United States Patent [19]

Fogarty

[11] Patent Number: 4,537,183

[45] Date of Patent: Aug. 27, 1985

[54] CONNECTOR DEVICE FOR CONNECTING ELASTIC TUBING OF AN IMPLANTABLE DEVICE

[75] Inventor: Terence M. Fogarty, Lakeland, Minn.

[73] Assignee: Mentor Corporation, Minneapolis, Minn.

[21] Appl. No.: 483,186

[22] Filed: Apr. 8, 1983

[51] Int. Cl.³ .............................................. A61F 5/00
[52] U.S. Cl. ..................................... 128/79; 128/1 R; 128/DIG. 25; 285/242; 285/DIG. 22
[58] Field of Search ......... 128/1 R, 79, 344, DIG. 25; 3/1; 604/228, 283, 284; 285/242, 255, DIG. 22

[56] References Cited

U.S. PATENT DOCUMENTS

| | | | |
|---|---|---|---|
| 409,066 | 8/1889 | Ravenel | 285/243 |
| 1,195,581 | 8/1916 | Hachmann | 285/246 |
| 1,204,352 | 11/1916 | Hachmann | 285/246 |
| 1,448,615 | 3/1923 | Deibert | 285/243 |
| 1,517,553 | 12/1924 | Fraser | 285/244 |
| 3,174,777 | 3/1965 | Lodholm et al. | 285/252 |
| 3,560,028 | 2/1971 | Ohba | 285/255 |
| 3,695,632 | 10/1972 | Kruse | 285/255 |
| 3,833,246 | 9/1974 | Wake | 285/247 |
| 3,853,122 | 12/1974 | Strauch et al. | 128/79 |
| 3,868,130 | 2/1975 | Schwertner et al. | 285/243 |
| 3,885,819 | 4/1975 | Egerer | 285/255 |
| 3,954,102 | 5/1976 | Buuck | 128/79 |
| 4,009,711 | 3/1977 | Uson | 128/79 |
| 4,201,202 | 5/1980 | Finney et al. | 128/79 |
| 4,235,227 | 11/1980 | Yamanaka | 128/79 |
| 4,238,132 | 12/1980 | Palmaer | 285/255 |
| 4,313,628 | 2/1982 | Duenke | 285/115 |
| 4,318,396 | 3/1982 | Finney | 128/79 |
| 4,321,911 | 3/1982 | Offutt | 285/242 |
| 4,343,498 | 8/1982 | Campanini | 285/174 |
| 4,451,070 | 5/1984 | Sauer | 285/242 |

FOREIGN PATENT DOCUMENTS 156470 12/1952 Australia .............................. 285/255

OTHER PUBLICATIONS

"An Implantable Fluid Transfer System for Treatment of Impotence", *Journal of Biomechanics*, vol. 5, pp. 557–570, Nov. 1972, by Kothari, Timm, Frohrib and Bradley.

"Management of Erectile Impotence, Use of Implantable Inflatable Prostheses", *Urology*, vol. II, No. 1, pp. 80–82, Jul. 1973 by Scott, Bradley and Timm.

"The Inflatable Penile Prosthesis by American Medical Systems", A Brochure Distributed by American Medical Systems, Inc., 3312 Gorham Avenue, Minneapolis, Minnesota 55426.

*Primary Examiner*—Stephen C. Pellegrino
*Assistant Examiner*—Mark D. Rooney
*Attorney, Agent, or Firm*—Kinney & Lange

[57] ABSTRACT

A connector device fluidly connects first and second sections of a highly elastic, highly compressible tubing of an implantable device such as an implantable penile prosthesis. The connector device includes a rigid connector component having a longitudinal main body with a fluid passage extending between first and second ends. The outer surface of the connector component includes a center surface section and first and second frusto-conical surfaces disposed at the first and second ends. The frusto-conical surfaces increase in diameter towards the center section, until the frusto-conical surfaces are larger in diameter than the center section. The tubing elastically engages the frusto-conical surfaces and a clamp surrounds the tubing preventing the tubing from "creeping" off the frusto-conical surfaces.

9 Claims, 7 Drawing Figures

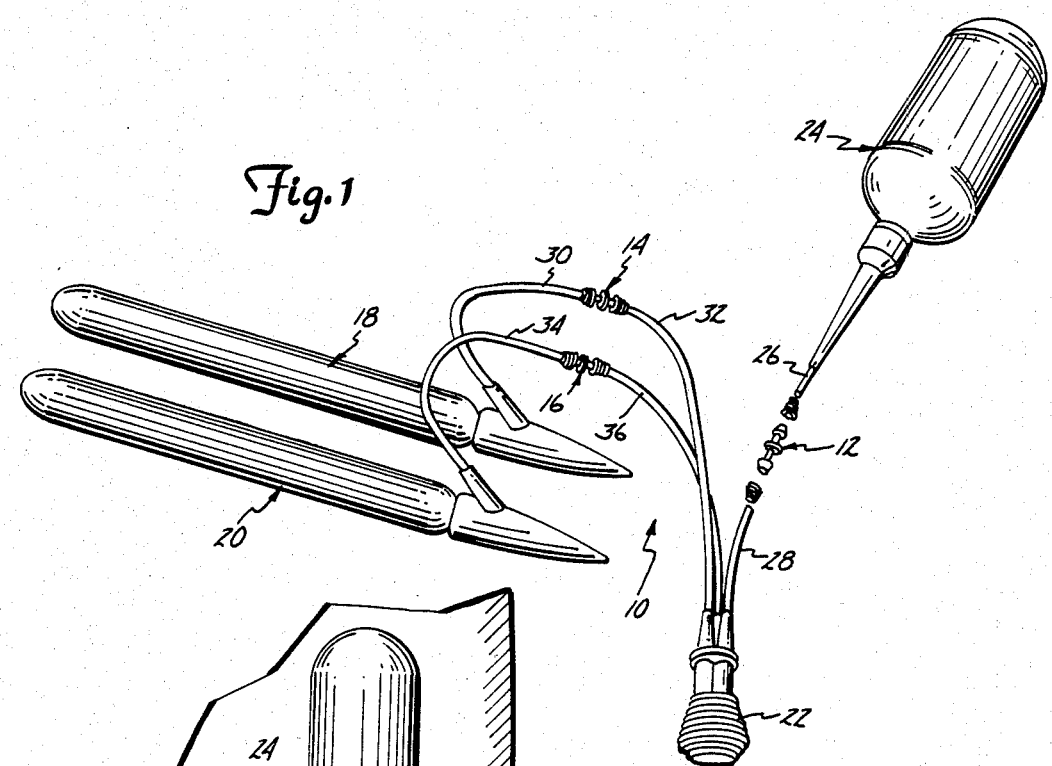
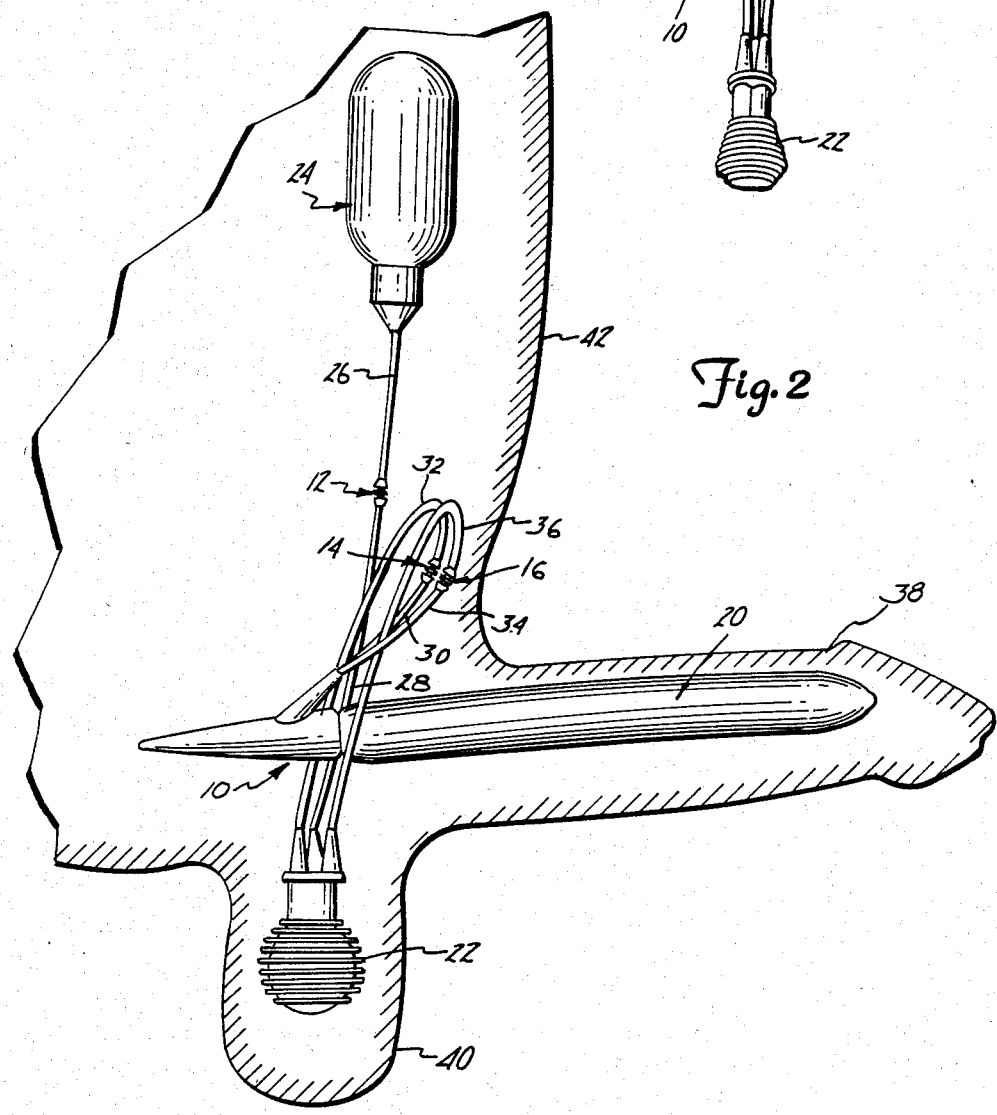

U.S. Patent  Aug. 27, 1985  Sheet 2 of 2  4,537,183
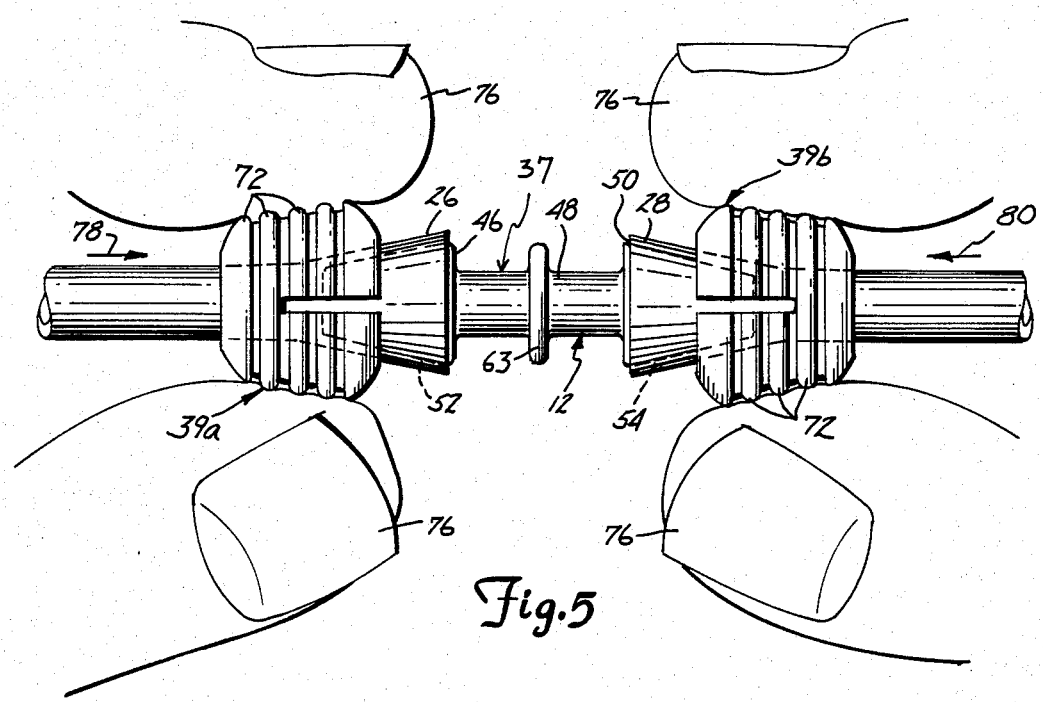
Fig.5
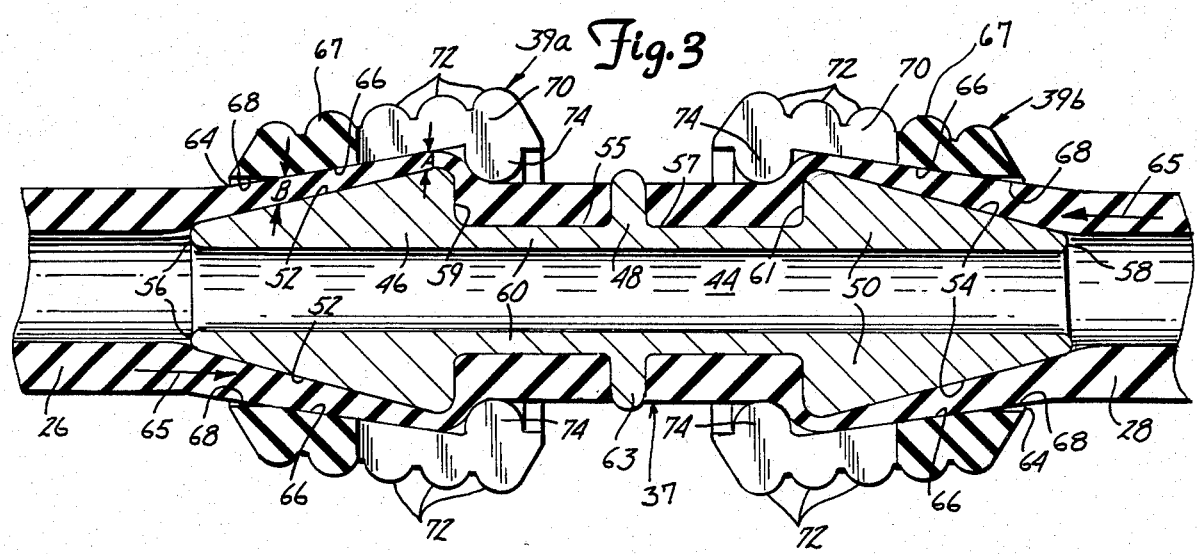
Fig.3
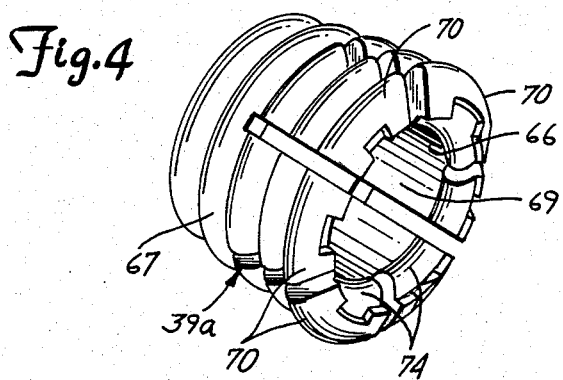
Fig.4
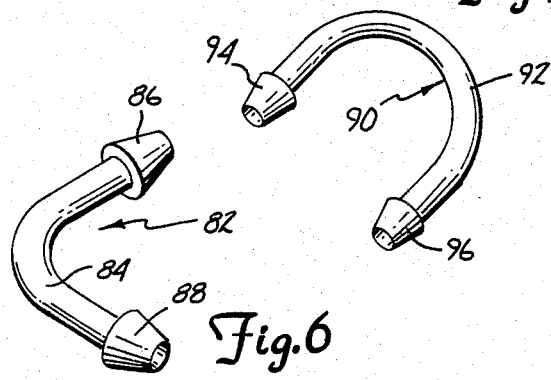
Fig.7
Fig.6

CONNECTOR DEVICE FOR CONNECTING ELASTIC TUBING OF AN IMPLANTABLE DEVICE

REFERENCE TO CO-PENDING APPLICATIONS

Reference is hereby made to the commonly assigned co-pending patent application filed on even date herewith entitled, "Penile Prosthesis Device," U.S. Ser. No. 483,184.

BACKGROUND OF THE INVENTION

1. Field of the Invention

The present invention relates to connectors that fluidly connect highly elastic, highly compressible tubing used with implantable devices; and in particular, the present invention relates to connectors that fluidly connect tubing in hydraulic implantable penile prostheses.

2. Description of the Prior Art

Sexual impotence caused by failure to achieve erection of the penis is a common problem. When the impotence is organic in origin, surgeons have attempted to duplicate the function of the erectile tissue (coropora cavernosa) in the penis by way of surgically implanted prostheses. The function of the penile prosthesis is to provide an artificial erection.

One type of penile prothesis presently being used is a hydraulic-type prosthesis having a generally tubular-shape member with flexible walls for implantation in the corpora cavernosa. The prosthesis is inflated by using a fluid drawn from a reservoir. As the prosthesis is inflated, the penis changes from a flaccid state to an erect state, mimicking normal erection. Several prior art hydraulic prostheses for implantation in the corpora cavernosa are described in the following patents: Strauch et al U.S. Pat. No. 3,853,122, Uson U.S. Pat. No. 4,009,711, Finney et al U.S. Pat. No. 4,201,202, Yamanaka U.S. Pat. No. 4,235,227, Finney U.S. Pat. No. 4,318,396, Buck U.S. Pat. No. 3,954,102 and in the articles entitled "An Implantable Fluid Transfer System for Treatment of Impotence," in the *Journal of Biomechanics* by Kothari, Timm, Frohrib, and Bradley, vol. 5, pp. 567-570, Nov. 1972 and "Management of Erectile Impotence, Use of Implantable Inflatable Prosthesis," in *Urology* by Scott, Bradley and Timm, Volume II, Number 1, pp. 80-82, July 1973. In addition, in the application entitled, "Penile Prosthesis Device," filed on even date with the present application, a unique hydraulic penile prosthesis device is described.

In the more recent embodiments of inflatable prostheses, the fluid used to inflate the prosthetic member is transferred from a reservoir through tubing to the prosthetic member. It is desirable that the several elements, such as the reservoir, pump and prosthetic members be implanted separately. Typically, sections of elastic tubing are permanently attached to each of the elements. These sections of tubing must then be attached to each other to fluidly connect the several elements after the elements have been implanted.

The tubing used in implantable devices is typically highly elastic and highly compressive. One method of connecting such tubing is to connect each free end of the tubing sections to a rigid connector. The tubing is pushed and expanded over the connector body with the fluid passages of the tubing communicating through the fluid passage of the connector. One such connector being presently used in connecting highly elastic, highly compressive tubing sections is a stainless steel connector having a constant diameter with ends having a rounded annular protrusion. Ends of the tubing sections are slid over the connector and sutured together. There are several problems with such a connector system. First, the tubing varies in quality from batch to batch and the physician must adjust the suturing technique to the variability of the tubing. Second, suturing of the tubing to connect the tubing sections increases the time of the implantation which is undesirable. Third, hydraulic pressurization of the tubing results in radial and longitudinal expansion of the tubing which increase the diameter and reduce the wall thickness of the tubing. Suturing of the tubing can be ineffective because the tubing is held on the connector by a narrow band of force which is intended to restrain movement of the tubing on the connector. The suture does not prevent the increase in diameter of the tubing adjacent the suture nor the reduction of wall thickness at the suture which results in reduced radial compressive forces applied by the tubing against the connector. The combination of reduced gripping due to reduced compressive forces and the longitudinal forces in the tubing can drive the tubing free off the connector.

Conventional clamping devices that compressively clamp tubing against a connector also have been found to be unsatisfactory for extended periods of time. Since the tubing is highly compressive along with being highly elastic, conventional clamps, regardless of the compressive force produced, still allow tubing to "creep" off the rigid connector over an extended period of time. If the tubing "creeps" off the connector, unnecessary surgery is required to correct the situation.

SUMMARY OF THE INVENTION

The present invention includes a connector device for fluidly connecting first and second sections of highly elastic, highly compressive tubing, such as is used with implantable devices that are implanted in humans. The connector device includes a rigid connector component that includes a longitudinal main body having first and second ends and a fluid passage extending between the first and second ends. On an outer surface, the connector component includes a center surface section having a first diameter and first and second frusto-conical surface sections disposed proximate the first and second ends. The diameter of each of the frusto-conical surfaces increases until it is larger than the diameter of the center surface section producing a drop-off surface section to the center surface section.

A clamp for retaining the tubing on the connector has an inner frusto-conical surface defining a cavity. An opening at one end of the clamp permits a section of the tubing to coaxially extend through the cavity. The clamp has a plurality of resilient fingers which flex outwardly engaging the outer surface of the tubing extending through the cavity. The tubing is connected to the connector component by grasping the clamp and pushing the tubing over one of the frusto-conical surfaces of the connector component using the clamp. The resilient fingers flex outwardly as the tubing and clamp are positioned over the frusto-conical surface until the ends of the fingers are positioned over the center surface section. The clamp provides a force component parallel to the longitudinal axis of the connector component which holds the tubing against the frusto-conical surface in a direction parallel to the longitudinal axis of the connector component and prevents the tubing from creeping off the connector component over an extended period of time.

BRIEF DESCRIPTION OF THE DRAWINGS

FIG. 1 is a perspective view of the connector of the present invention used in an implantable prosthesis device;

FIG. 2 is a partial sectional view of a portion of the human body with the implanted prosthesis device shown whole;

FIG. 3 is an enlarged cross sectional view of the connector of the present invention;

FIG. 4 is a perspective view of the clamp used in the connector of the present invention;

FIG. 5 is an elevational view illustrating the method of attaching the tubing with the connector;

FIG. 6 is a perspective view of a portion of an alternative embodiment of the connector of the present invention; and FIG. 7 is a perspective view of a portion of another alternative embodiment of the connector of the present invention.

DETAILED DESCRIPTION OF THE PREFERRED EMBODIMENTS

An implantable penile prosthesis, generally indicated at 10 in FIG. 1, includes a connector device of the present invention generally indicated at 12, 14 and 16. The penile prothesis includes two prosthetic members 18 and 20, a pump 22 and a fluid reservoir 24. Elastic tubing sections 26, 28 fluidly connect the fluid reservoir 24 with the pump 22; elastic tubing sections 30, 32 fluidly connect the prosthetic member 18 with the pump 22; and elastic tubing sections 34, 36 fluidly connect the prosthetic member 20 to the pump 22. The penile prosthesis is described in detail in an application entitled "Penile Prosthesis Device," filed on even date with the present application which is herein incorporated by reference.

The connector devices 12, 14 and 16 fluidly connect the tubing sections described above to each other. For example, the connector device 12 connects the tubing section 26 with the tubing section 28, connecting the reservoir 24 with the pump 22. Similarly, the connector device 14 connects the tubing section 32 with the tubing section 30 connecting the pump 22 with the prosthetic member 18; and the connector device 16 connects the tubing section 36 with the tubing section 34 connecting the pump 22 with the prosthetic member 20.

As illustrated in FIG. 2, the implantable penile prosthesis 10 of the present invention is adapted for implantation in a male to correct erectile impotence. The prosthetic members 18 and 20 (only member 20 being visible in FIG. 2) are implanted within a dilated corpora cavernosa of a penis 38. The pump 22 is implanted in a scrotal sac 40 and the reservoir 24 is positioned above the prosthetic members 18 and 20 behind an abdominal wall 42.

The implantable prosthesis 10 provides an artificial erection to an impotent male. The pump 22 located in the scrotal sac 40 is squeezed manually by the user to pump fluid from the reservoir 24 into the prosthetic members 18 and 20 distending and enlarging the members 18 and 20 to cause an erection.

As stated previously, the connector devices 12, 14 and 16, as illustrated in FIG. 1, connect the appropriate tubing sections so that the reservoir 24, pump 22, and prosthetic members 18 and 20 are fluidly connected.

The unique configuration of the connector devices permit easy connection of the tubing sections while securely retaining the tubing sections in place for an extended period of time. The tubing sections must be held securely in place for an extended period of time since the implantable device 10 is implanted and any readjustment of the tubing connection would require further surgery.

The tubing sections are typically made of a highly elastic and highly compressive polymer such as a silicone polymer. Prior to the present invention, there have been problems in retaining the tubing in a connected state since the tubing, when stretched over a connector, creeps back to its original unstretched state and off the connector over extended periods of time. It has been found that the tubing creeps off the connector due to hydraulic loadings which cause the tubing to be stretched radially with the tubing desiring to return to an unstretched state.

The structure of the connector device of the present invention is best seen in FIG. 3 wherein the connector device 12 is shown in an enlarged cross-sectional view. Although only the connector device 12 is shown in enlarged view, it should be understood that connector devices 14 and 16 are of the same construction.

The connector device 12 includes a rigid connector component 37 and left and right connector clamps 39a and 39b, respectively. The connector component may be made of any implantable grade material such as plastic, stainless steel, titanium or other metals. A preferred material is an AISI 316 L stainless steel.

The connector component 37 includes a fluid passage 44 that permits fluid to pass between tubing sections 26 and 28. The connector component 37 further includes a first tubing retaining section 46, a center flanged section 48 and a second tubing retaining section 50. The tubing retaining sections 46 and 50 have frusto-conical surfaces 52, 54, respectively, and the center section has generally cylindrical surfaces 55 and 57. The frusto-conical surfaces 52, 54 preferably are inclined approximately 10° to 15° with respect to the longitudinal axis of the connector component 37 with a preferred angle of approximately 13.5°. The frusto-conical surfaces 52 and 54 permit the elastic tubing to be slid easily over the tubing retaining sections 46 and 50. Although the tubing retaining sections are shown having the same diameters, tubing retaining sections having different diameters to connect tubing sections of different sizes are within the scope of the present invention. The ability to connect the tubing section is quite important since the tubing sections are connected during surgery after the reservoir, pump and prosthetic members have been implanted.

The tubing retaining sections 46 and 50 have end wall surfaces 56, 58, respectively, that are preferably rounded with a radius equal to one-half the thickness of the retaining sections proximate the end wall surface. The diameter of the passage 44 proximate the end wall surfaces 56, 58 is preferably approximately 15 percent smaller than the inside diameter of the tubing. The rounded end surfaces 56 and 58 not only facilitate the positioning of the tubing over the tubing retaining sections 46, 50, but greatly minimize the chances of the tubing being pierced while being connected. In addition, the rounded end surfaces in combination with the approximately 15 percent smaller passage 44 minimize possible damage to the tubing by the end surfaces when the tubing is flexed in a longitudinal direction.

The frusto-conical surfaces 52 and 54 increase in diameter toward the center flanged section 48 until the diameter of the frusto-conical surfaces is greater than the diameter of the center flanged section 48. The point of difference in diameter between the frusto-conical surface and the center flanged section is defined by drop-off surface sections 59, 61 which are substantially perpendicular to the surfaces 55 and 57.

The tubing sections 26 and 28 are pushed to stretch over the tubing retaining sections 46, 50, respectively, until a portion of the tubing extends past the drop-off sections 59, 61. The tubing contracts to elastically engage the surfaces 55, 57 of the center flanged section 48.

The center flanged section 48 preferably includes an annular flange 63 which serves as a separation and a stop between the tubing sections 26 and 28. The tubing sections 26 and 28 are positioned to preferably abut against the annular flange 63.

The tubing sections 26 and 28 are positioned over the respective tubing retaining sections 46 and 50 and held in position by the tubing clamps 39a and 39b. The clamp 39a and 39b are preferably of one-piece construction, either of machined or molded plastic, preferably polysulfone.

The clamps 39a and 39b provide compressive forces in two directions. First, the clamps provide a compressive force that is substantially perpendicular to a longitudinal axis of the connector. However, as discussed previously with regard to the prior art, perpendicular compressive forces have been found to be unsatisfactory in retaining highly elastic and highly compressive tubing over extended periods of time. Second, and most importantly, the clamp provides a force component in a direction substantially parallel to the longitudinal stretching of the tubing as indicated by arrows 65 in FIG. 3.

It has been found by the applicant that highly elastic and highly compressive tubing is retainable over extended periods of time if a force is applied to the tubing in a plane substantially parallel to the orientation of stretching. The tubing is stretched, not only in the axial direction, but also in the longitudinal direction when positioned over the tubing retaining sections 46 and 50. The clamps 39a and 39b are used to position the tubing onto the tubing retaining sections and provide a compressive force in a direction that opposes the "creeping" of the tubing off the connector component 37.

The clamps 39a and 39b are of the same construction and like reference characters will be used to indicate like elements. Referring to FIG. 3, the clamps 39a and 39b have an integral body 67 with an opening 64 disposed at a rearward end. The tubing extends through the opening 64 and through a cavity 69. The clamps have an inner frusto-conical surface 66 defining the cavity 69. The surface 66 cooperates with the frusto-conical surfaces 52 and 54 in securing the tubing sections 26 and 28 over the respective tubing retaining sections. The frusto-conical surface 66 has a slightly different incline than the frusto-conical surfaces 52 and 54 to take into account the thinning of the tubing that occurs as the tubing is stretched and expanded over the frusto-conical surfaces 52 and 54. The frusto-conical surface 66 is disposed at an angle with the longitudinal axis of the connector such that the distance between the frusto-conical surfaces 52, 54 and the frusto-conical surface 66 of the clamp decreases as the tubing thins. For example, the distance "A" between the frusto-conical surface 66 of the clamp and the frusto-conical surface 52 proximate the drop-off section 59 is less than the distance "B" proximate the opening 64.

Preferably, the distance between the inner surface of the clamp and the outer surface of the tubing retaining section not only accommodates the thinned tubing, but the frusto-conical surface 66 is disposed to slightly compress the tubing along the entire tubing retaining section. The frusto-conical surface 66 compresses the tubing approximately five percent (5%) at the rearward end of the clamp proximate the opening 64 and two percent (2%) proximate the forward end.

The conical surface 66 preferably has an outer edge portion 68 which defines a diameter of a constant dimension of the opening 64. The constant dimension diameter eliminates possible pinching of the tubing and swelling as it exits the opening 64, further minimizing the tubing over an extended period of time.

Referring to FIG. 4 wherein only clamp 39a is illustrated, the clamp 39a has flexible fingers 70 that flex outwardly when the tubing and clamps are positioned over the tubing retaining sections. The fingers 70 retract back to a normal position when the clamps 39a and 39b are positioned over the tubing retaining sections.

Each finger 70 has an inwardly-projecting spur 74 positioned at a forward end of each finger 70. When the clamps 39a and 39b are positioned over the respective tubing retaining section and tubing, the spurs 74 engage the tubing adjacent the drop-off surfaces 59 and 61 to prevent the clamps from sliding off, as illustrated in FIG. 3.

Preferably, the clamps have a plurality of outwardly projecting ribs 72 on an exterior surface. The purpose of the ribs 72 is to aid in manually pushing the clamps 39a and 39b onto the tubing retaining section.

The ends 56 and 58 of the connector component extend past the opening of the clamps 39a and 39b, leaving a portion of the tubing surrounding the tubing retaining sections free of the clamps 39a and 39b. When the tubing flexes at the end of the connector component, the tubing flexes about the rounded ends 56 and 58 which minimizes wear of the tubing over an extended period of time. In one successful embodiment, the distance that the connector component extends past the clamp opening has ranged approximately 0.0100 inches to 0.0200 inches using tubing having an approximate outer diameter of 1/8 inches and an inner diameter of approximately 1/16 inches.

The method of connecting the tubing sections 26 and 28 with the connector 12 is illustrated in FIG. 5. First, the tubing sections 26 and 28 are positioned onto the frusto-conical surfaces 52, 54 of the tubing retaining sections 46, 50, respectively. The tubing is positioned over the tubing retaining sections so that the ends of the tubing are proximately aligned with the drop-off surfaces 59 and 61.

The clamps 39a and 39b are gripped manually by fingers 76 and pushed in a direction towards each other indicated by arrows 78 and 80. Pushing the clamps 39a and 39b towards each other, moves the tubing 26 and 28 over the edge of the tubing retaining sections and drop-off surfaces 59 and 61. The tubing is pushed until it preferably abuts against the flange 63 and the clamp spurs 74 and contracts around the drop-off surfaces 59 and 61 and surfaces 55 and 57.

Alternative embodiments of the connector device are illustrated in FIGS. 6 and 7. The alternative embodiments provide a physician with a choice of connector configurations for different situations. The clamps 39a and 39b are compatible with the connectors shown in FIGS. 6 and 7.

In FIG. 6, the connector of the present invention has a right angle configuration and is generally indicated at 82. The connector 82 has no central annular ring 48, as the connector 12 previously described, and has a longer center section 84 with tubing retaining sections 86 and 88 disposed on opposite ends of the center section. The center section is bent approximately 90°.

In FIG. 7, the connector of the present invention is in a U-shaped configuration and is generally indicated at 90. The center section 92 of the connector 90 is U-shaped with each of the legs of the "U" including a tubing retaining section 94 and 96.

CONCLUSION

The connector device of the present invention provides a secure connection over an extended period of time of highly elastic, highly compressive tubing which is used in fluidly connecting various components of implantable devices. In addition, the connector device facilitates easy connection of tubing sections during surgery and minimizes tubing wear due to flexing of the tubing proximate the end of the connector.

Although the present invention has been described with reference to the preferred embodiment, workers skilled in the art will recognize that the connector device can be used with other implantable devices and that changes may be made in form and detail without departing from the spirit and scope of the invention.

What is claimed is:

1. An implantable device for implantation in a living body, the device comprising:
    first implantable component means for implanting into a first portion of the body and having a fluid reservoir;
    second implantable component means for implanting into a second portion of the body spaced from the first portion of the body, the second component means having a fluid chamber;
    a first section of elastic tubing fixedly attached at one end to the first implantable component means;
    a second section of elastic tubing fixedly attached to the second implantable component means; and
    a connector device for fluidly connecting the first and second sections of elastic tubing, each tubing section having an outer surface with an outer diameter and an inner surface with an inner diameter, the connector comprising:
        a main body having first and second ends and a connector fluid passage extending between the first and second ends, a center surface section having an outer diameter, and first and second frusto-conical surface sections disposed proximate the first and second ends with the maximum diameter of the first and second frusto-conical surface sections being greater than the outer diameter of the center surface sections, the first and second frusto-conical surface sections frictionally engaging the inner surface of the first and second sections of tubing, respectively; and
        first and second clamps, each clamp having a body with an inner substantially smooth frusto-conical surface defining a cavity, the cavity having a forward and a rearward end with a opening at least equal to the outer diameter of the tubing, said opening being defined by a cylindrical surface portion of a constant diameter contiguous with the inner frusto-conical surface, the tubing extending through the opening and the cavity, and the inner frusto-conical surface engaging the outer surface of the tubing which is located over the frusto-conical surface of the connector device so that a compressive force is exerted on the tubing between the inner frusto-conical surface of the clamp and the outer frusto-conical surface of the connector, in a direction opposing any creeping of the tubing section and retaining tubing on the frusto-conical surface section and wherein the first clamp has a plurality of flexible fingers proximate the forward end and wherein at least one of the fingers has an inwardly projecting spur for retaining the clamp in position over the tubing and the first frusto-conical surface, said spur being positioned at a forward end of the finger such that the spur is disposed between the first frusto-conical surface and the center surface section of the main body.

2. The device of claim 1 wherein the connector fluid passage has an inside diameter of approximately 15% less than the inner diameter of the first and second tubing sections.

3. The device of claim 1 wherein the first and second ends each have a generally curved end wall surface whose radius is approximately equal to one-half the thickness of the main body proximate the respective end wall surface.

4. The device of claim 1 wherein the inner frusto-conical surface of the clamp is sloped at an incline different than the incline of the first frusto-conical surface section of the connector such that a change in thickness of the tubing is accommodated.

5. The device of claim 1 wherein the clamp has a plurality of ridges on an outer surface.

6. The device of claim 5 wherein the ridges are disposed in a tapered arrangement, the arrangement being tapered toward the rearward end to facilitate placement of the clamp in position.

7. The device of claim 1 wherein the center section includes an outwardly extending annular ring.

8. A connector device for fluidly connecting first and second sections of elastic tubing of an implantable device, each tubing section fixedly attached at one end to first and second fluid retaining implantable components, each tubing section having an outer surface with an outer diameter and an inner surface with an inner diameter, the device comprising:
    a main body having a center portion and first and second ends and a connector fluid passage extending between the first and second ends and through the center portion, the first end having a first outer tapered surface tapering to a diameter sufficiently small to permit the first section of elastic tubing to be stretched thereover, said section of first tubing elastically engaging the first tapered surface in a longitudinally stretched state; and
    at least a first clamping means for imparting a force component oriented in a longitudinal direction and for engaging the outer surface of the first section of tubing which is located over the frusto-conical surface of the connector device, so that the force component is directed on the tubing between the inner frusto-conical surface of the clamp and the outer frusto-conical surface of the connector to oppose the tubing from contracting off the first tapered surface, retaining the first section of tubing on the first tapered surface, said first clamping means including a body with an inner substantially smooth frusto-conical surface defining a cavity, the cavity having a forward and a rearward end with an opening at the rearward end, said opening being defined by a cylindrical surface portion of a constant diameter contiguous with the inner frusto-conical surface and at least one flexible finger proximate the forward end having an inwardly projecting spur for retaining the clamp in position over the tubing and the first outer tapered surface, said spur being positioned at a forward end of the finger such that the spur is disposed between the first tapered surface and the center surface section of the main body.

9. The connector device of claim 8 wherein the second end includes a second outer tapered surface tapering to a diameter sufficiently small to permit the second section of the elastic tubing to be stretched thereover, said section of second tubing elastically engaging the second tapered surface in a longitudinally stretched state, and further including a second clamping means for imparting a force component oriented in a longitudinal direction and for engaging the outer surface of the tubing so that the force component is directed to oppose the tubing from contracting off the second tapered surface, retaining the second section tubing on the second tapered surface, said second clamping means including a body with an inner substantially smooth frusto-conical surface defining a cavity, the cavity having a forward and a rearward end with an opening at the rearward end, said opening being defined by a cylindrical surface portion of a constant diameter contiguous with the inner frusto-conical surface and at least one flexible finger proximate the forward end having an inwardly projecting spur for retaining the clamp in position over the tubing and the second outer tapered surface, said spur being positioned at a forward end of the finger such that the spur is disposed between the second tapered surface.

* * * * *